(12) United States Patent
Sharpless et al.

(10) Patent No.: US 6,852,874 B2
(45) Date of Patent: Feb. 8, 2005

(54) SECOND CYCLE ASYMMETRIC DIHYDROXYLATION REACTION

(75) Inventors: K. Barry Sharpless, La Jolla, CA (US); Malin Andersson, Gothenburg (SE); Robert Epple, La Jolla, CA (US); Valery Fokin, Carlsbad, CA (US)

(73) Assignee: The Scripps Research Institute, La Jolla, CA (US)

( * ) Notice: Subject to any disclaimer, the term of this patent is extended or adjusted under 35 U.S.C. 154(b) by 164 days.

(21) Appl. No.: 09/941,410

(22) Filed: Aug. 28, 2001

(65) Prior Publication Data

US 2002/0042545 A1 Apr. 11, 2002

Related U.S. Application Data

(60) Provisional application No. 60/237,554, filed on Oct. 2, 2000.

(51) Int. Cl.[7] .............................................. C07C 205/00
(52) U.S. Cl. ........................... 560/23; 560/60; 568/811; 568/860
(58) Field of Search ................................. 568/811, 860; 560/23, 60

(56) References Cited

U.S. PATENT DOCUMENTS

| 4,965,364 | A | * | 10/1990 | Marko |
| 5,516,929 | A | * | 5/1996 | Sharpless |
| 6,297,186 | B1 | * | 10/2001 | Kobayashi |
| 6,387,033 | B1 | * | 5/2002 | Choudary |

FOREIGN PATENT DOCUMENTS

WO    WO-89/02428    *   3/1989

OTHER PUBLICATIONS

Jacobsen, et al., "Asymmetric Dihydroxylation via Ligand–Accelerated Catalysis", *J. Am. Chem. Soc. 110*: 1968–1970 (1988).

Jacobsen, et al., "Kinetic Role of the Alkaloid Ligands in Asymmetric Dihydroxylation", *J. Am. Chem. Soc. 111*: 737–739 (1989).

Wai, J. S. M., et al., "A Mechanistic Insight Leads to a Greatly Improved Osmium–Catalyzed Asymmetric Dihydroxylation Process", *J. Am. Chem. Soc. 111*: 1123–1125 (1989).

Lohray, et al., "Documenting the Scope of the Catalytic Asymmetric Dihydroxylation", *Tetrahedron Lett. 30*: 2041–2044 (1989).

Kwong, et al., "Preclusion of the 'Second Cycle' in the Osmium–Catalyzed Asymmetric Dihydroxylation of Olefins Leads to a Superior Process", *Tetrahedron Lett. 31*: 2999–3002 (1990).

Sharpless, et al., "The Osmium–Catalyzed Asymmetric Dihydroxylation: A New Ligand Class and a Process Improvement", *J. Org. Chem. 57*: 2768–2771 (1992).

Morikawa, et al., "Catalytic Asymmetric Dihydroxylation of Tetrasubstituted Olefins", *J. Am. Chem. Soc. 115*: 8463–8464 (1993).

Kolb, et al., "Catalytic Asymmetric Dihydroxylation", *Chem. Rev. 94*: 2483–2547 (1994).

Norrby, et al., "Toward an Understanding of the High Enantioselectivity in the Osmium–Catalyzed Asymmetric Dihydroxylation. 3. New Insights into Isomeric Forms of the Putative Osmaoxetane Intermediate", *J. Am. Chem. Soc. 118*: 35–42 (1996).

Rudolph, et al., "Smaller Substituents on Nitrogen Facilitate the Osmium–Catalyzed Asymmetric Aminohydroxylation", *Angew. Chem. Int. Ed. Engl. 35*: 2810–2813 (1996).

DelMonte, et al., "Experimental and Theoretical Kinetic Isotope Effects for Asymmetric Dihydroxylation. Evidence Supporting a Rate–Limiting "(3+2)" Cycloaddition", *J. Am. Chem. Soc. 119*: 9907–9908 (1997).

Kolb, H. C.; Sharpless, K. B. "Asymmetric Dihydroxylation" in *"Transition Metals for Organic Synthesis: Building Blocks and Fine Chemicals"*, vol. 2, Wiley–VCH; New York, 1998: Beller, M.; Bolm, C., Eds. pp. 219–242.

Kolb, H. C.; Sharpless, K. B. "Asymmetric Aminohydroxylation" in *"Transition Metals for Organic Synthesis: Building Blocks and Fine Chemicals"*, vol. 2, Wiley–VCH; New York, 1998: Beller, M.; Bolm, C., Eds. pp. 243–260.

* cited by examiner

Primary Examiner—Michael L. Shippen
(74) Attorney, Agent, or Firm—Donald G. Lewis

(57) ABSTRACT

A process for catalyzing asymmetric dihydroxylations of olefins employs an Os(VI) complex as a catalytic intermediate in the formation of chiral vicinal diol products. The process requires a chiral bidentate ligand that favors diol formation in the "second cycle" of asymmetric dihydroxylation.

11 Claims, 6 Drawing Sheets

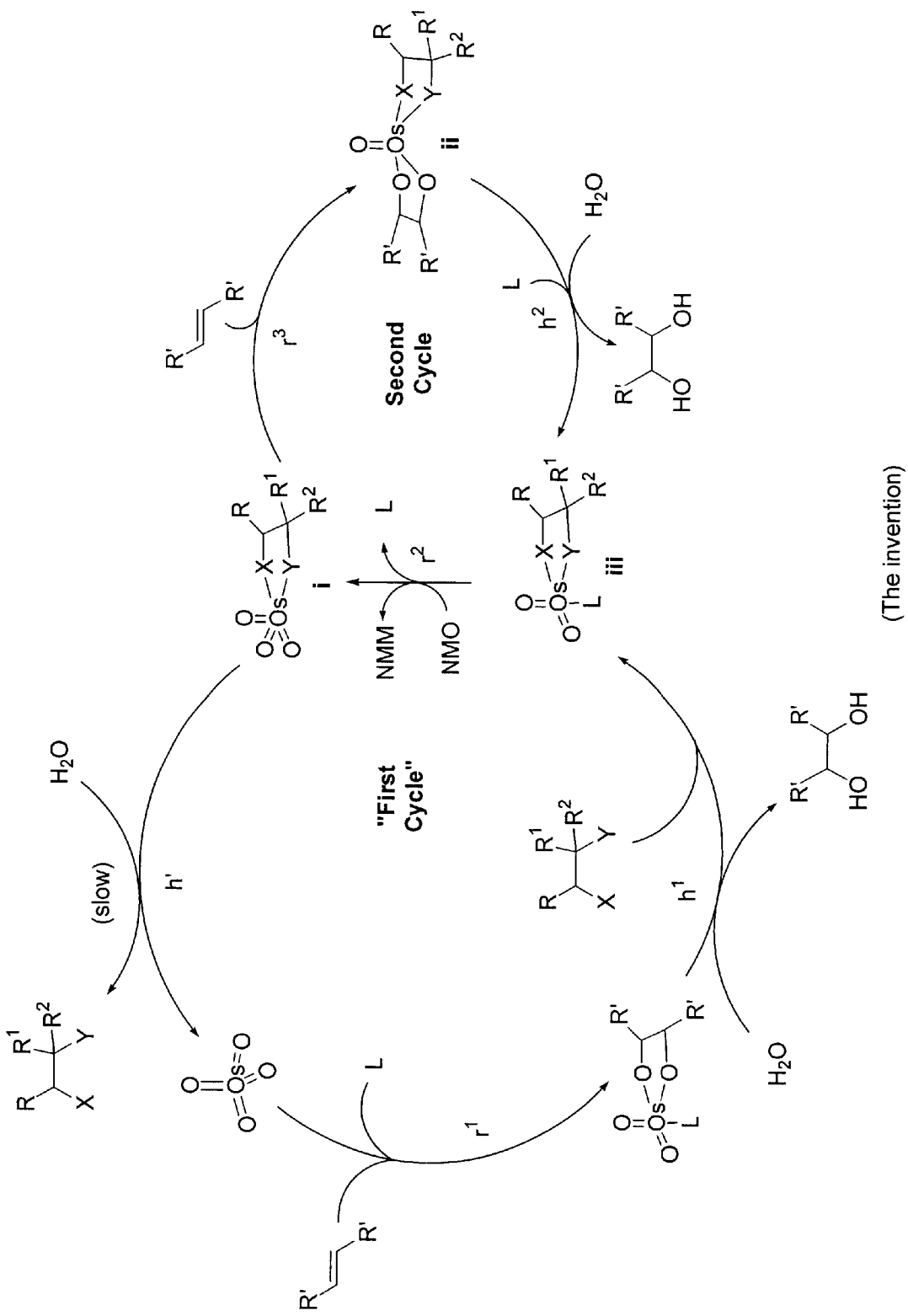
Figure 1b (The invention)

| Ligand | Ligand, mol% | Conversion,% | ee,% (abs. conf.) |
|---|---|---|---|
|  1 | 5<br>2 | ≥99<br>≥99 | 25 (R)<br>25 (R) |
|  2 | 5 | ≥99 | 7 (R) |
|  3 | 5 | >99 | 29 (R) |
|  4 | 5<br>2 | ≥ 99<br>≥ 99 | 42 (R)<br>42 (R) |
|  5 | 5 | 99 | 5 (R) |
|  6 | 5 | 99 | 25 (S) |

SECOND CYCLE ASYMMETRIC DIHYDROXYLATION REACTION

STATEMENT OF GOVERNMENT RIGHTS

This invention was made with government support under a National Institutes of Health Grant No. GM-28384. The government has certain rights in the invention.

FIELD OF THE INVENTION

The invention relates to osmium catalyzed dihydroxylations of olefins. More particularly, the invention relates to osmium catalyzed second cycle asymmetric dihyroxylations of olefins.

BACKGROUND

Osmium-catalyzed asymmetric dihydroxylation (AD) of olefins using cinchona alkaloid-derived ligands has proven to be a highly effective and reliable process across nearly the entire range of olefin types and substitution patterns on both laboratory and industrial scales (Kolb, H. C.; et al. *Chem. Rev.*, 1994, 94, 2483–2547; H. C. Kolb, K. B. Sharpless, in *Transition Met. Org. Synth.*, Vol 2, (Eds. M. Beller, C. Bolm), Wiley-VCH, Weinheim, 1998, 219–242).

The most helpful mechanistic insight in osmium catalysts, from the viewpoint of these process improvement endeavors developing the AD, was the realization that there are two catalytic cycles producing diol (FIG. 1A) (Wai, J. S. M.; et al. *J. Am. Chem. Soc.* 1989, 111, 1123). In homogeneous conditions, when N-methylmorpholine N-oxide (NMO) is employed as a reoxidant, the second cycle, leading to the reduced enantioselectivities, dominates because two possible hydrolysis steps, $h^1$ and $h^2$ are much slower than the three red-ox steps, $r^1$, $r^2$, and $r^3$. As a consequence, the Os(VI) bisglycolate (ii) becomes the most stable, resting form of the catalyst.

It is known that certain classes of olefins exhibit unique reactivity in the osmium-catalyzed aminohydroxylation and dihydroxylation (Rubin A. E.; Sharpless, K. B. *Angew. Chem. Int. Ed. Engl.* 1997, 36, 2637–2640; Pringle, W.; Sharpless, K. B. *Tetrahedron Lett.* 1999, 40, 5150–5154; Fokin, V. V.; Sharpless, K. B. *Angew. Chem. Intl. Ed. Eng.*, 2001, in press). Unlike most substrates, these special olefins undergo rapid and nearly quantitative conversion to aminoalcohols and diols, correspondingly, with very low catalyst loading in the absence of added ligands and with only one equivalent of the oxidant. This is in sharp contrast to other olefins, whose turnover is crucially dependent on the Ligand Acceleration Effect (for a review of ligand accelerated catalysts, see Berrisford, D. J.; et al. *Angew. Chem. Int. Ed. Engl.* 1996, 35, 451–454). The more recently, the remarkable reactivity of unsaturated carboxylic acids has been characterized (Fokin, V. V.; Sharpless, K. B. *Angew. Chem. Intl. Ed. Eng.*, 2001, in press).

In all of the above special cases, only racemic products are formed, even when a chiral ligand is added in large excess. This and other available evidence (H.-T. Chang, Ph.D. dissertation, The Scripps Research Institute, 1997.) suggest that these olefins turn over almost exclusively in the $2^{nd}$ catalytic cycle, where osmium (VI) bis(glycolate) (ii) (or the bis (azaglycolate) in case of aminohydroxylation) is the most stable intermediate—so stable that it is the only detectable osmium complex present under steady-state conditions. According to the current mechanistic hypothesis, proximal carboxylate groups facilitate the hydrolysis of this complex, which is the rate-determining step. This explains the dramatically increased reactivity of these substrates.

Although it is desirable to avoid the $2^{nd}$ cycle at all costs, deleterious as it is to enantioselectivity, the enticing possibilities it offers for a new way to control osmium(VIII) catalysis have been clear since the time of its discovery in 1982. Although early attempts to obtain enantioselectivity with $2^{nd}$ cycle ligands failed, the recent enormous jump in effectiveness of the $2^{nd}$ cycle systems (Rubin A. E.; Sharpless, K. B. *Angew. Chem. Int. Ed. Engl.* 1997, 36, 2637–2640; Pringle, W.; Sharpless, K. B. *Tetrahedron Lett.* 1999, 40, 5150–5154) has shown that its inherent advantages may be exploited to develop new catalytic processes. To gain control over the $2^{nd}$ cycle, one needs to design a ligand that (a) is chiral and capable of controlling stereochemistry in the olefin oxidation step $r^3$; (b) aids in the hydrolytic release ($h^2$) of the product from the Os(VI) complex (ii) formed by oxidation of olefin; and (c) is not itself hydrolytically removed from the osmium coordination sphere. This restriction is not really so severe—it only has to dominate the catalysis. This can be achieved with a mobile ligand too (e.g., ligand-accelerated catalysis or simply equilibrium favoring the desired osmium complex in the olefin oxidation step).

SUMMARY

One aspect of the invention is directed to a process for catalyzing an asymmetric dihydroxylation reaction for converting an olefin substrate to a chiral vicinal diol product. The process employs the step of mixing the olefin substrate under reaction conditions with a catalytic amount of osmium, a stoichiometric amount of N-methylmorpholine oxide as a co-oxidant, and a suitable amount of chiral bidentate ligand for ligating, together with the olefin substrate, to the osmium for forming an Os(VI) complex as a catalytic intermediate to the formation of the chiral vicinal diol product.

Another aspect of the invention is directed to a process for catalyzing a second cycle dihydroxylation reaction for converting an alkene substrate to a chiral vicinal diol product. The process employs the step of mixing the alkene substrate under reaction conditions with a catalytic amount of osmium, a stoichimetric amount of N-methylmorpholine oxide as a co-oxidant, and a suitable amount of chiral ligand for facilitating the asymmetric dihydroxylation reaction. The chiral ligand is represented by the following structures:

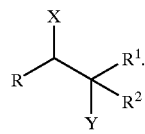

In the above structure, R is a radical selected from hydrogen, carboxylate, phenyl, 1-naphthyl, 2-naphthyl, alkyl (C1–C12), cyclo-alkyl (C3–C12), carbamoyl, N-alkyl (C1–C12) carbamoyl, or N, N-alkyl(C1–C12) carbamoyl. The phenyl, 1-naphthyl, and 2-naphthyl radicals may optionally have substituents in any available position. $R^1$ is a radical selected from carboxylate, carbamoyl, N-alkyl (C1–C12) carbamoyl, or N,N-dialkyl(C1–C12) carbamoyl. $R^2$ is a radical selected from H, alkyl(C1–C12), aryl, or heteroaryl. X and Y are radicals independently selected from hydroxyl, amino, N-alkyl(C1–C12)sulfonylamino, N-arylsulfonylamino, or N-heteroarylsulfonylamino. In one of the preferred modes, the chiral ligand is an α-hydroxy-β-N-sulfonyl-amino acid. In another of the preferred modes, the chiral ligand is an β-hydroxy-α-N-sulfonyl-amino acid. Good results can often be achieved if the reaction is carried out with 1 mol % to 10 mol % in chiral ligand. However, 5 mol % of chiral ligand is more usual. The range for the osmium concentration is between 0.1 mol % and 1 mol %.

However, an osmium concentration of 0.2 mol % is more usual. The best olefin substrates are often electron deficient. The optimal pH for the reaction mixture is often approximately 5.

BRIEF DESCRIPTION OF DRAWINGS

FIG. 1B illustrates the first cycle and second cycle of asymmetric dihydroxylation when using these "second cycle" ligands.

DETAILED DESCRIPTION

Described here are the first ligands found to induce asymmetry in the osmium-catalyzed dihydroxylation proceeding in the $2^{nd}$ catalytic cycle. As a simple model for screening the ligand candidates shown in the table of FIG. 5, the dihydroxylation of styrene under the Upjohn conditions is used. It is noteworthy that overoxidation of the product diol, a fairly common side reaction in the Upjohn dihydroxylation, was not observed.

Figure 2:
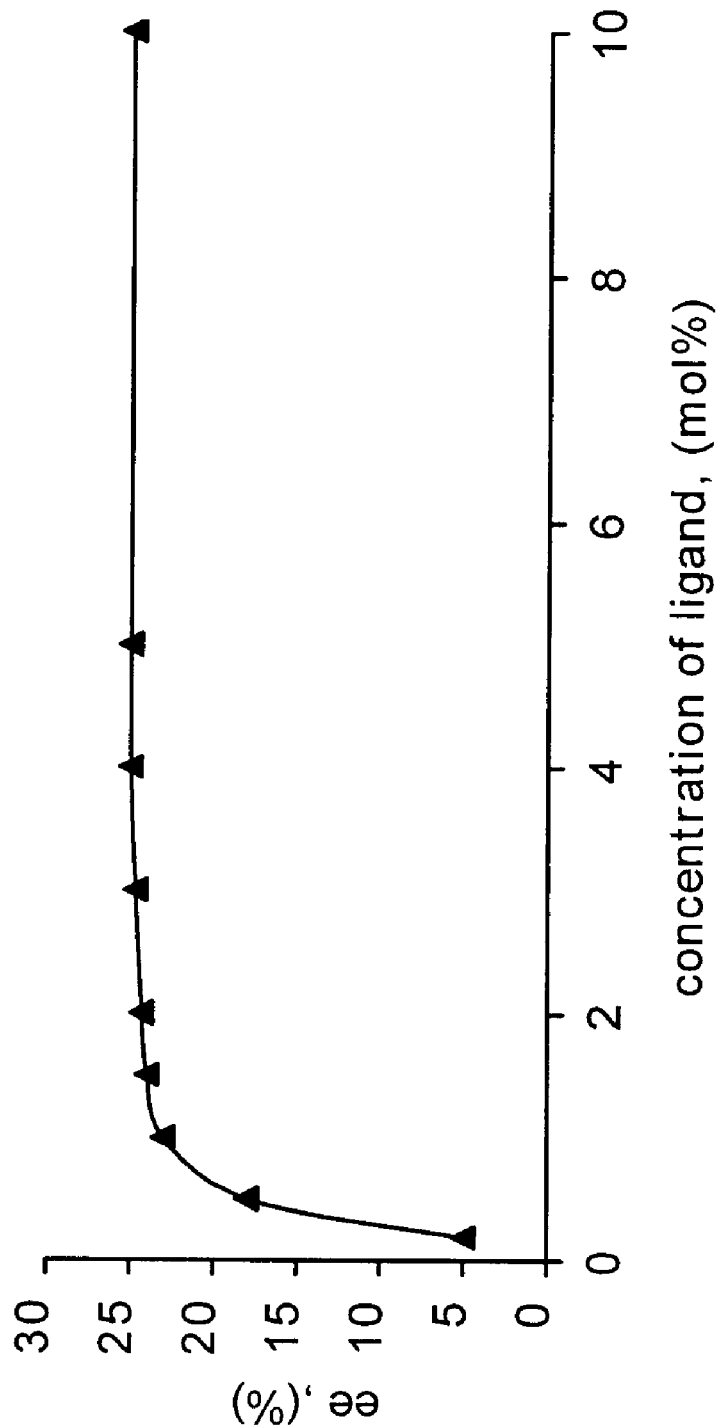
FIG. 2 illustrates a graph of percent ee of product as a function of the amount of ligand used. The ee's remained constant throughout the course of reactions and, more importantly, as low as 1.5–2 mol % ligand was sufficient to attain the ceiling ee.

Even such simple ligand as tartaric acid, although needed in 25 mol % quantity, showed some asymmetric induction. Finding a ligand with a higher affinity for osmium was an obvious requirement to reduce the amount of ligand. Since N-sulfonyl-1,2-hydroxyamines (vicinal hydroxysulfonamides) have much higher binding constants for osmium than analogous 1,2-diols, a number of N-toluenesulfonyl derivatives of α,β-hydroxyaminoacids were screened resulting in the improvement of the ee to 42%. The ee's remained constant throughout the course of reactions and, more importantly, as low as 1.5–2 mol % ligand was sufficient to attain the ceiling ee (FIG. 2). To ensure that the maximum possible ee afforded by each ligand was observed, 5 mol % of ligand was routinely used. It has been demonstrated from different examples that 1.5–2.0 mol % is sufficient. The finding that dependence of the enantioselectivity on the amount of the ligand shows saturation behavior points to the fact that the process in its present form operates at the maximum ee afforded by the ligand.

Simple structure-activity studies have revealed that a free carboxylate group appears to be an essential component of a successful ligand. Thus, only racemic diol was obtained when the methyl ester of 1 was used as a ligand. Location of the HO— and TsNH—groups was found to play an important role as well. For example, the phenylisoserine-based ligand 1 afforded higher ee than its regioisomer 2. The absolute configuration of the diol products appears to be determined by the stereochemistry of the α-carbon of the ligand (cf. entries 1, 3 and 6). Additional investigations have shown that modification of the substituents on the sulfonamide group (R—$SO_2NH$—) has only a minor effect on the stereochemical outcome of the reaction. However, the ligand should preferentially contain an N-sulfonyl moiety, as its replacement with an amide (as in 5) or a carbamate resulted in very low to no enantioselectivity.

Figure 3:
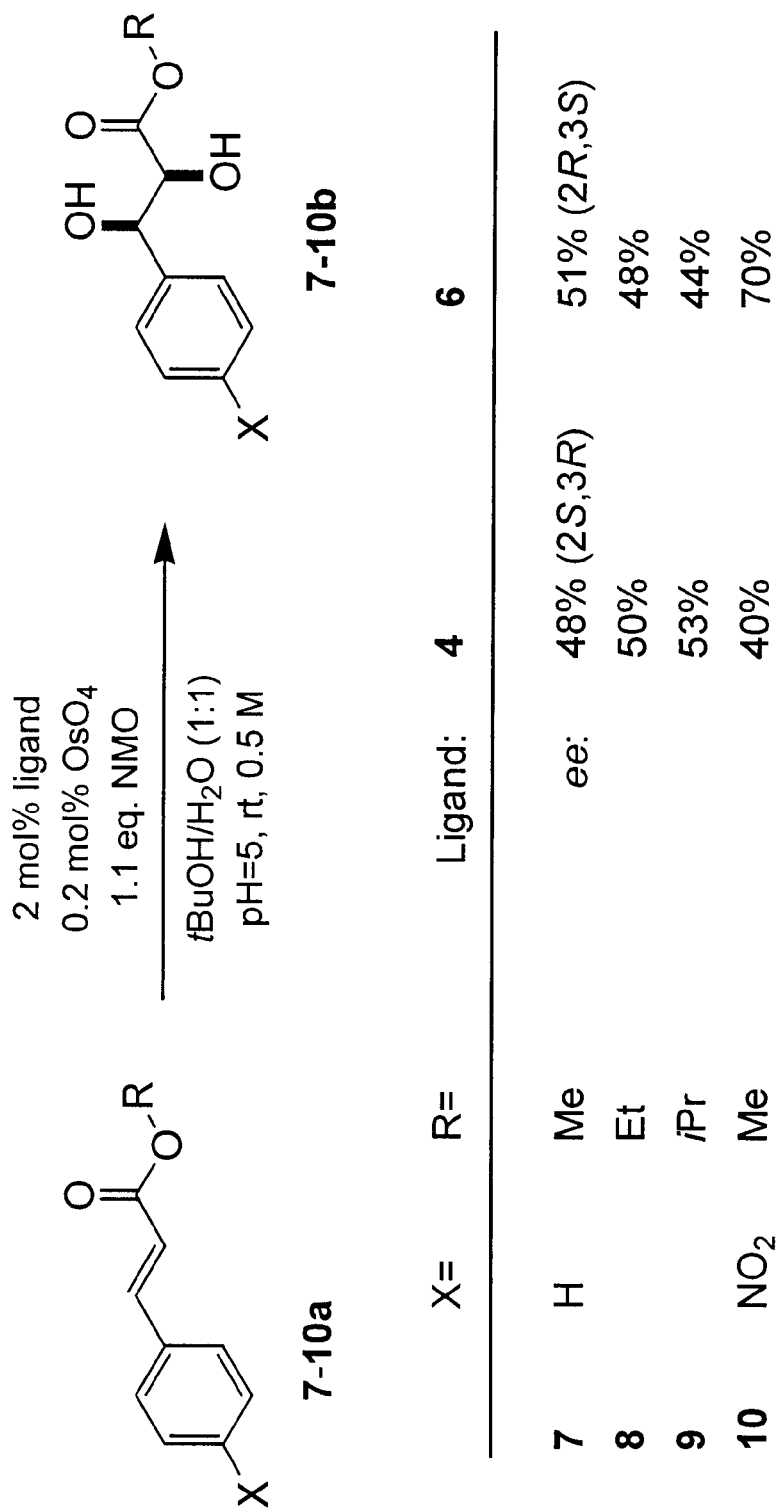
FIG. 3 illustrates a reaction using N-(p-toluenesulfonyl) threonine (2S,3R)-6 which has been found to be particularly effective for dihydroxylation of cinnamate esters, with 70% ee realized in one case.

Most of the ligands discussed above can be readily prepared in enantiomerically enriched form using previously developed catalytic olefin transformations (Li, G.; et al. Angew. Chem. Int. Ed. Engl. 1996, 35, 451–454; H. C. Kolb, K. B. Sharpless, in Transition Metals for Fine Chemicals and Organic Synthesis, Vol. 2 (Eds.: M. Beller, C. Bolm), Wiley-VCH, Weinheim, 1998, 243–260; G. Schlingloff, K. B. Sharpless, in Asymmetric Oxidation Reactions: A Practical Approach, (Ed.: T. Katsuki), Oxford University Press, Oxford, in press). Furthermore, some hydroxyaminoacids are commercially available compounds, and can be easily converted to their corresponding N-sulfonyl derivatives (Brenner, M.; et al. Helv. Chim. Acta, 1951, 36, 2102–2106). For example, N-(p-toluenesulfonyl) threonine (2S,3R)-6 has been found to be particularly effective for dihydroxylation of cinnamate esters, with 70% ee realized in one case (FIG. 3). Acidification of the reaction mixture with sulfuric or acetic acid to approximately pH 5 considerably accelerates the reaction without jeopardizing the enantioselectivity.

Accordingly, it is demonstrated herein that confining the osmium-catalyzed asymmetric dihydroxylation to the $2^{nd}$ catalytic cycle is a viable concept. The exemplary processes disclosed herein provide to modest to good enantioselectivities. However, the concept of the invention is broader than the examples and offers many variables for optimization. The $2^{nd}$ cycle-based osmium-catalyzed oxidations disclosed herein facilitates the asymmetric oxidation of olefins that were heretofor difficult to oxidize.

Experimental Procedure:

Typical dihydroxylation procedure as exemplified on methyl 4-nitro-cinnamate: 4-nitrocinnamic acid methyl ester (207 mg, 1 mmol) and N-(4-toluenesulfonyl)-(L)-threonine (13.6 mg, 5 mol %) (Brenner, M.; et al. Helv. Chim. Acta, 1951, 36, 2102–2106) were dissolved in 6 ml of 1:1 tBuOH/ $H_2O$ mixture. NMO (50 wt % in water, 228 μl, 1.1 mmol) and $OSO_4$ (0.1M in acetonitrile, 20 μl, 0.002 mmol) were added successively. The pH was adjusted to 5 by addition of 150 μl 2N $H_2SO_4$, and the reaction mixture was stirred vigorously for 24 hrs, at which time the pH was adjusted to 5 again. After additional 24 hrs (≧98% conversion by LC), methyl (2R,3S)-(+)-2,3-dihydroxy-3-(p-nitrophenyl)-propionate (Denis, J. A.; et al. J. Org. Chem. 1990, 55, 1957) was obtained in 70% ee (HPLC: Chiralcel OG, 20% iPrOH/ hexane). The reaction time can be reduced to ca. 24 hrs by maintaining constant pH using a pH-stat. A 10 mmol scale reaction, performed under similar conditions, afforded product as white solid in 75% yield (1.8 g) and 70% ee. Recrystallization from ethanol produced needle-shaped crystals in 57% yield and 81% ee.

Figure 1A:
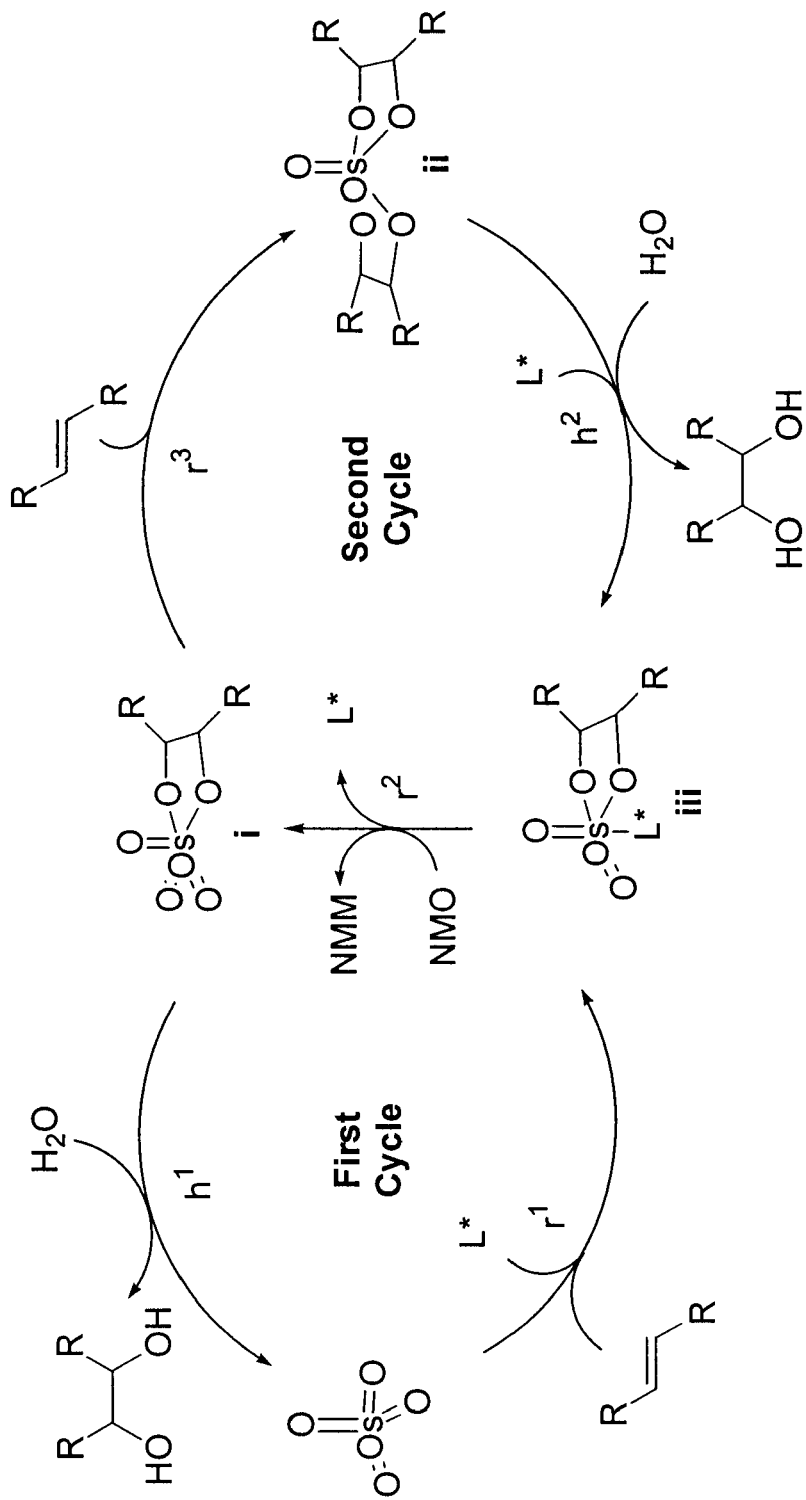
FIG. 1A illustrates the first cycle and second cycle of asymmetric dihydroxylation.

Detailed Description of Figures:

FIG. 1A illustrates the first cycle and second cycle of asymmetric dihydroxylation. There are two catalytic cycles producing diol. In homogeneous conditions, when N-methyl-morpholine N-oxide (NMO) is employed as a reoxidant, the second cycle, leading to the reduced enantioselectivities, dominates because two possible hydrolysis steps, $h^1$ and $h^2$ are much slower than the three red-ox steps, $r^1$, $r^2$, and $r^3$. As a consequence, the Os (VI) bisglycolate(ii) becomes the most stable, resting form of the catalyst.

FIG. 1B illustrates the first cycle and second cycle of asymmetric dihydroxylation. There are two catalytic cycles producing diol. In this diagram, the "first cycle" is not entered unless the ligand is hydrolyzed off of the osmium in step h'. "L" in the diagram can represent any monodentate ligand species in the reaction mixture.

FIG. 2 shows a graph of percent ee of product as a function of the amount of ligand used. The ee's remained constant throughout the course of reactions and, more importantly, as low as 1.5–2 mol % ligand was sufficient to attain the ceiling ee.

FIG. 3 shows a reaction using N-(p-toluenesulfonyl) threonine (2S,3R)-6 which has been found to be particularly effective for dihydroxylation of cinnamate esters, with 70% ee realized in one case. N-sulfonyl-1,2-hydroxyamines (vicinal hydroxysulfonamides) have much higher binding constants for osmium than analogous 1,2-diols, a number of N-toluenesulfonyl derivatives of a,b-hydroxyaminoacids were screened resulting in the improvement of the ee to 42% (in the dihydroxylation of styrene).

Figure 4:
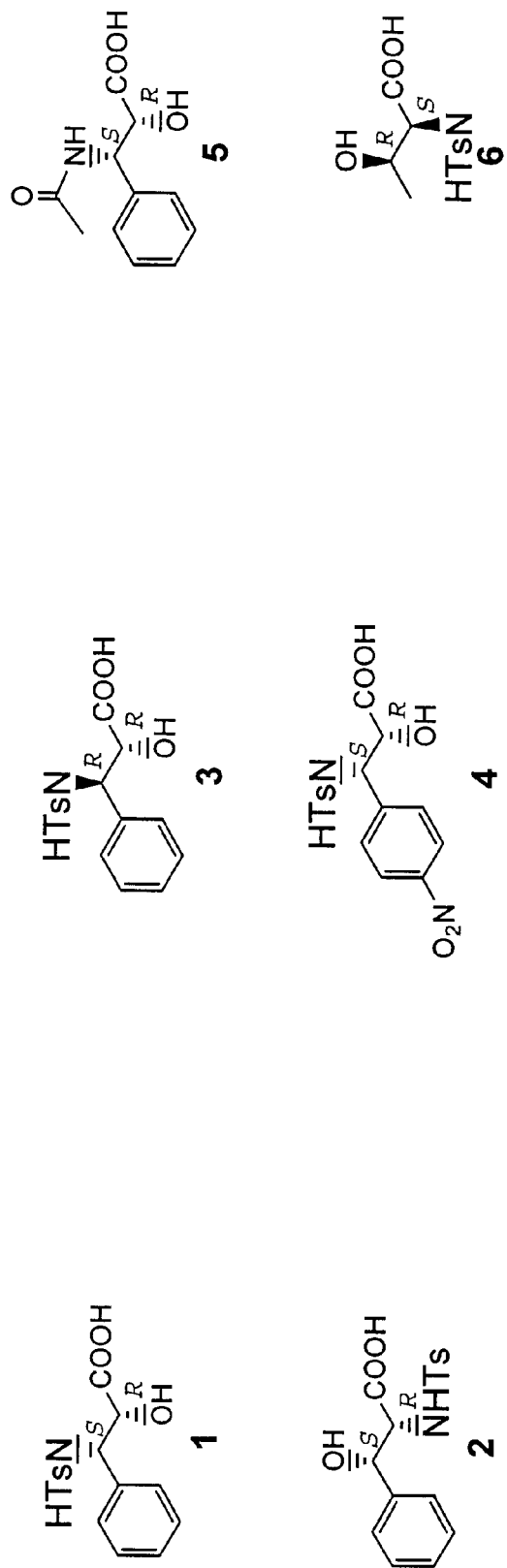
FIG. 4 illustrates the structures of preferred chiral ligands.

FIG. 4 shows the structures of the ligands examined. Simple structure-activity studies have revealed that a free carboxylate group appears to be an essential component of a successful ligand. Thus, only racemic diol was obtained when the methyl ester of 1 was used as a ligand. Location of the HO— and TsNH—groups was found to play an important role as well. For example, the phenylisoserine-based ligand 1 afforded higher ee than its regioisomer 2. The absolute configuration of the diol products appears to be determined by the stereochemistry of the α-carbon of the ligand (cf. entries 1, 3 and 6). Additional investigations have shown that modification of the substituents on the sulfonamide group (R—SO$_2$NH—) has only a minor effect on the stereochemical outcome of the reaction. However, the ligand should preferentially contain an N-sulfonyl moiety, as its replacement with an amide (as in 5) or a carbamate resulted in very low to no enantioselectivity.

Figure 5:
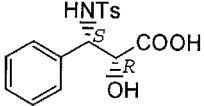
FIG. 5 illustrates a table that shows dihydroxylation of styrene with novel ligands.
Figure 5:
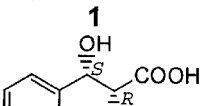
Figure 5:
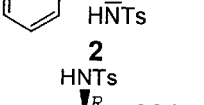
Figure 5:
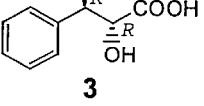
Figure 5:
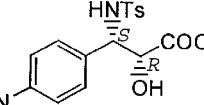
Figure 5:
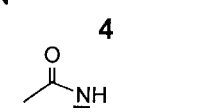

FIG. 5 is a table that shows dihydroxylation of styrene with novel ligands. All reactions were performed on 1 mmol scale at 0.5 M concentration in tBuOH/H$_2$O (1:1) with 1.1 eq. NMO and 0.2 mol % of OsO$_4$. The progress was monitored by GC and ees were determined by HPLC (Chiralcel OB, 10% iPrOH/Hexane); the absolute configuration of styrene diol was assigned by comparison with authentic samples.

What is claimed is:

1. A process for catalyzing a second-cycle asymmetric dihydroxylation reaction for converting an olefin substrate to a chiral vicinal diol product, said process comprising the following steps:

Step A: mixing the olefin substrate with a catalytic amount of a chiral bidentate ligand in an aqueous solvent, the aqueous solvent optionally being an alcohol/water solvent mixture, the chiral bidentate ligand being represented by the following structure:

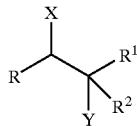

wherein:
R is a radical selected from the group consisting of hydrogen, carboxylic acid, phenyl, 1-naphthyl, 2-naphthyl, alkyl($C_1$–$C_{12}$), cyclo-alkyl($C_3$–$C_{12}$), carbamoyl, N-alkyl($C_1$–$C_{12}$) carbamoyl, and N,N-alkyl ($C_1$–$C_{12}$) carbamoyl, wherein the phenyl, 1-naphthyl, and 2-naphthyl radicals ay optionally have substituents in any available position;
$R_1$ is a radical selected from the group consisting of carboxylic acid, carbamoyl, N-alkyl($C_1$–$C_{12}$) carbamoyl, and N,N-dialkyl($C_1$–$C_{12}$) carbamoyl;
$R_2$ is a radical selected from the group consisting of hydrogen, alkyl($C_1$–$C_{12}$), aryl, and heteroaryl; and
X and Y are radicals independently selected from the group consisting of hydroxyl, amino, N-alkyl($C_1$–$C_{12}$) sulfonylamino, N-arylsulfonylamino, and N-heteroarylsulfonylamino;

with the following provisos:
if X is not a hydroxyl group, then Y must be a hydroxy group;
if Y is not a hydroxyl group then X must be a hydroxyl group; and
at least one of the following must be a carboxylic acid group: R, $R_1$ or $R_2$; and then Step B: adding to the mixture of said Step A a stoichiometric amount or a stoichimetric excess of N-methyl morpholine N-oxide with respect to the olefin substrate and a catalytic amount of osmium tetraoxide under reaction conditions for catalyzing the second-cycle asymmetric dihydroxylation reaction for converting the olefin substrate to the chiral vicinal diol product.

2. A process according to claim 1 where the chiral bidentate ligand is selected from the group represented by the following structures:

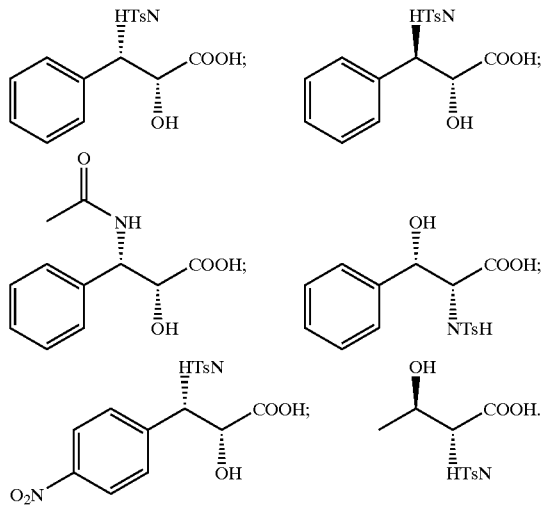

3. A process according to claim 1 wherein the chiral ligand is an α-hydroxy-β-N-sulfonylamino carboxylic acid.

4. A process according to claim 1 wherein the chiral ligand is an α-N-sulfonylamino-β-hydroxy carboxylic acid.

5. A process according to claim 1 wherein chiral bidentate ligand has a concentration between 1 mol % and 10 mol %, with respect to the olefin substrate.

6. A process according to claim 5 wherein, in said Step A, the chiral bidentate ligand has a concentration of 5 mol %, with respect to the olefin substrate.

7. A process according to claim 6 wherein, in said Step B, the osmium tetraoxide has a concentration of between 0.1 mol % and 1 mol %, with respect to the olefin substrate.

8. A process according to claim 7 wherein, in said Step B, the osmium tetraoxide has a concentration of approximately 0.2 mol %, with respect to the olefin substrate.

9. A process according to claim 8, wherein the olefin substrate is an α,β-unsaturated carboxylic acid ester.

10. A process according to claim 9 wherein the pH of the reaction mixture of said Step B is approximately 5.

11. A process according to claim 10 wherein the alcohol used in the alcohol/water solvent mixture of said Step A is tertiary butyl alcohol.

* * * * *